(12) United States Patent
Lee

(10) Patent No.: US 8,673,639 B2
(45) Date of Patent: Mar. 18, 2014

(54) METHODS FOR ISOLATING STEM CELLS

(76) Inventor: Hee Young Lee, Gunsan-si (KR)

(*) Notice: Subject to any disclaimer, the term of this patent is extended or adjusted under 35 U.S.C. 154(b) by 0 days.

(21) Appl. No.: 13/509,757

(22) PCT Filed: Nov. 23, 2009

(86) PCT No.: PCT/KR2009/006890
§ 371 (c)(1),
(2), (4) Date: Jul. 17, 2012

(87) PCT Pub. No.: WO2011/062313
PCT Pub. Date: May 26, 2011

(65) Prior Publication Data
US 2012/0276629 A1    Nov. 1, 2012

(30) Foreign Application Priority Data

Nov. 17, 2009    (KR) .................. 10-2009-0111080

(51) Int. Cl.
*C12N 5/00* (2006.01)
*B04B 1/00* (2006.01)
*A61M 37/00* (2006.01)
*A61M 1/00* (2006.01)

(52) U.S. Cl.
USPC ............ 435/381; 422/548; 604/82; 604/316; 604/319

(58) Field of Classification Search
USPC ........... 604/320, 131, 190, 542, 319, 403, 82; 210/380, 781; 435/325, 381
See application file for complete search history.

(56) References Cited

U.S. PATENT DOCUMENTS

| | | | | |
|---|---|---|---|---|
| 3,596,652 | A * | 8/1971 | Winkelman | 600/575 |
| 4,197,735 | A * | 4/1980 | Munzer et al. | 73/61.68 |
| 6,659,995 | B1 * | 12/2003 | Taheri | 604/500 |
| 7,179,391 | B2 * | 2/2007 | Leach et al. | 210/782 |
| 7,588,732 | B2 * | 9/2009 | Buss | 422/501 |
| 2003/0168480 | A1 | 9/2003 | Kim | |
| 2006/0224144 | A1 | 10/2006 | Lee | |
| 2007/0148766 | A1 * | 6/2007 | Yoshimura et al. | 435/325 |
| 2008/0167613 | A1 * | 7/2008 | Khouri et al. | 604/119 |

FOREIGN PATENT DOCUMENTS

| | | |
|---|---|---|
| JP | 2007-289076 A | 11/2007 |
| KR | 10-0472577 B1 | 2/2005 |
| KR | 10-0473363 B1 | 3/2005 |
| KR | 10-0473568 B1 | 3/2005 |
| KR | 10-2009-0129069 A | 12/2009 |
| KR | 2009-0129069 A | 12/2009 |
| WO | 2011/062313 A1 | 5/2011 |

* cited by examiner

*Primary Examiner* — Taeyoon Kim
*Assistant Examiner* — Srikanth Patury
(74) *Attorney, Agent, or Firm* — Sughrue Mion, PLLC

(57) ABSTRACT

Disclosed is a method for isolating stem cells. The method uses a specially designed apparatus including: a container containing an aspirate; a piston having an outer diameter corresponding to the inner diameter of the container and having at least one through-hole; and a connection tube adapted to feed an enzyme or a washing solution into the container through the through-hole, having a tip connected to the through-hole, and connected to an external tube or another container containing the enzyme or washing solution at the other end thereof. The method includes pulling the piston backward to form a negative pressure in the container containing the aspirate and to allow the enzyme or washing solution to enter the container containing the aspirate through the connection tube and the through-hole of the piston.

8 Claims, 4 Drawing Sheets

METHODS FOR ISOLATING STEM CELLS

CROSS REFERENCE TO RELATED APPLICATIONS

This application is a National Stage of International Application No. PCT/KR2009/006890 filed Nov. 23, 2009, claiming priority based on Korean Patent Application No. 10-2009-0111080 filed Nov. 17, 2009, the contents of all of which are incorporated herein by reference in their entirety.

TECHNICAL FIELD

The present invention relates to methods for isolating stem cells from adipose tissue, and more specifically to methods for isolating stem cells under conditions where the opportunity to be exposed to air is minimized.

BACKGROUND ART

Stem cells have the ability to differentiate into two or more cell types while possessing the capacity of self-renewal. Studies are currently underway to harvest stem cells from adipose tissue as well as bone marrow. Adipose-derived stem cells isolated from adipose tissue are multipotent stem cells that have the ability to differentiate into various cell types, including adipocytes, myocytes, chondrocytes and osteocytes.

Adipose stem cells have the advantages of superior self-renewal capacity and easy culture ex vivo when compared to marrow-derived mesenchymal stem cells. Other advantages of adipose stem cells are that they can be isolated from abundant adipose tissue and can be harvested in a simple and safe manner. From a functional standpoint, adipose stem cells and marrow-derived mesenchymal stem cells were found to share almost the same characteristics, including multipotency, cytological characteristics, immunological characteristics and tissue regeneration. That is, adipose stem cells have been considered as possible replacements for mesenchymal stem cells and have proven their great usefulness in medical applications.

In comparison with mesenchymal stem cells, adipose stem cells are advantageous in easy and safe tissue acquisition and unlimited tissue supply and demand. In addition, adipose stem cells are easy to culture ex vivo. Due to these advantages, adipose stem cells may be considered in preference to marrow-derived mesenchymal stem cells in terms of tissue accessibility, stability, effectiveness and economic efficiency.

Many methods have been proposed to isolate and culture adipocytes. According to a typical method, after fat is sucked out or excised and crushed to pieces, its tissue is digested with collagenase, followed by centrifugation. Then, the sediment is collected and a stromal vascular fraction (SVF) is separated therefrom. The SVF is used for cell culture.

Further, according to the method disclosed in Korean Patent No. 788632, an adipose-containing suspension in physiological saline obtained from human adipose tissue by liposuction is homogeneously re-suspended in an appropriate amount of physiological saline, a proper amount of the resulting suspension is placed in a flask or roller bottle for cell culture, followed by stationary culture or roller bottle culture. In the case of stationary culture, the suspension is allowed to stand for at least 6 to 12 hours and then the cell layers attached on the surface of the flask are treated with trypsin and collected. At this time, the suspended matter is directly collected in a small amount of physiological saline and is used without further processing. Alternatively, when it is intended to reduce the volume of the cell layers, the cell layers collected in the physiological saline are subjected to centrifugation at 1000 rpm for 10 minutes and the settled pellet layers only are used. The separated cell layers contain adult stem cells and fibroblasts. The separated cell layers are mixed with fat to prepare a composition for skin care or plastic surgery. The composition contains adult stem cells, fibroblasts and fat or adipocytes.

On the other hand, PCT International Publication No. WO2005/042730 suggests a method for preparing stem cells without collagenase treatment, the method comprising: A) obtaining an aspirate by liposuction; B) transferring the aspirate to a centrifuge to obtain a cell fraction; C) subjecting the cell fraction to centrifugation by specific gravity; and D) collecting a cell layer with lower specific gravity than that of erythrocytes.

A container for enzymatic treatment and centrifugation that is currently used in clinical applications is in the form of a tube whose one end is completely closed and includes a stopper fastened to the outer surface of the tube on top thereof. When it is desired to move a content of the tube or to feed a washing solution into a container containing adipose-derived stem cells, a substance separated from the content is removed out of the tube or the washing solution enters the container in a state in which the tube is in an open position.

As such, adipose-derived stem cells as active ingredients are obtained by sucking out or excising fat, discharging it with a washing solution, followed by centrifugation. In addition, the active ingredients must be mixed with other ingredients for use in secondary applications.

Some serious problems may be caused in this course. The first problem is that it is not easy to actually isolate active ingredients by centrifugation. It is clinically known that 500 thousand cells can be isolated from about 100 cc of adipose tissue aspirate. This value corresponds to only about one millionth of the total number of cells. Accordingly, methods using centrifugation are inefficient. That is, it takes a long time for isolation by centrifugation and extreme conditions for isolation do great damage to effective cells.

Another problem is that in the course of the treatment of fat extracts, it is not easy to mix with other ingredients.

Another problem may be fatal. That is, during acquisition and isolation of fat and extraction, culture and reinfusion of active ingredients, cells may be exposed to the outside, posing the risk of microbial contamination. This problem adversely affects the safety of humans, such as side effects resulting from secondary infection or contamination.

Specifically, as soon as the stopper connected to the container is removed, active ingredients in the container come into contact with large quantity of air and may be contaminated by falling dirt and dust. In attempts to solve these problems, stem cells are clinically isolated in clean rooms of Class 1000 or above. However, much cost and time are required to ensure safety. In most cases, clinicians remove the isolated substances while identifying the layers with their eyes to separate the desired layer. In this course, loss of the active ingredients is inevitable.

DISCLOSURE

Technical Problem

The present invention has been made in an effort to solve the above problems, and it is an object of the present invention to provide a method for isolating stem cells in improved yield while minimizing damage to adipose tissue.

It is another object of the present invention to provide a method for isolating stem cells with improved stability while blocking the possibility of contamination under ambient atmospheric conditions.

Technical Solution

According to an aspect of the present invention, there is provided a method for isolating stem cells using an apparatus including: a container containing an aspirate; a piston having an outer diameter corresponding to the inner diameter of the container and having at least one through-hole; and a connection tube adapted to feed an enzyme or a washing solution into the container through the through-hole, having a tip connected to the through-hole, and connected to an external tube or another container containing the enzyme or washing solution at the other end thereof, wherein the method includes pulling the piston backward to form a negative pressure in the container containing the aspirate and to allow the enzyme or washing solution to enter the container containing the aspirate through the connection tube and the through-hole of the piston.

According to another aspect of the present invention, there is provided a method for isolating stem cells using an apparatus including: a container containing an aspirate; a piston having an outer diameter corresponding to the inner diameter of the container and having at least one through-hole; and a connection tube adapted to feed an enzyme or a washing solution into the container through the through-hole, having a tip connected to the through-hole, and connected to an external tube or another container containing the enzyme or washing solution at the other end thereof, wherein the method includes pushing the piston forward to form a positive pressure in the container and to allow a fluid rising in the piston to escape outside through the through-hole and the connection tube.

After centrifugation is performed to isolate stem cells as active ingredients from the mixture of the aspirate and the enzyme or washing solution, the piston is pushed forward to form a positive pressure in the container and to allow a fluid rising in the piston to escape outside through the through-hole and the connection tube.

The connection tube is connected to another container through a tube.

The apparatus further includes means for quantification control or a valve optionally connected to at least one container in a zone where the connection tube or the tube is connected to the another container.

The valve is a diaphragm one-way valve or a 3-way valve with Luer Lock.

The 3-way valve includes: a first valve connected to the connection tube or the tube; a second valve connected to the container containing the washing solution or a container adapted to extract active ingredients; and a third valve connected to a container adapted to extract ingredients to be removed or the container containing the washing solution.

Advantageous Effects

As is evident from the foregoing, the methods according to the embodiments of the present invention block the opportunity for an aspirate obtained by liposuction accommodated in the container to come into contact with the outside, so that adipose-derived stem cells can be effectively obtained while ensuring stability.

In addition, a syringe used for liposuction can be used to isolate adipose-derived stem cells, so that the cells can be protected against contamination, eventually leading to an improvement in yield.

MODE FOR INVENTION

Figure 1:
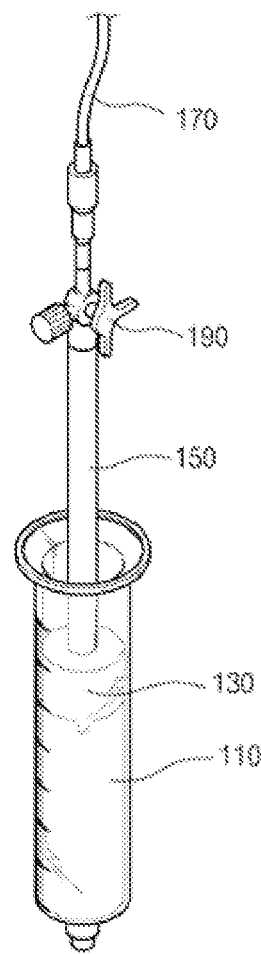
FIG. 1 is a perspective view of an apparatus for implementing a method according to a preferred embodiment of the present invention.
Figure 2:
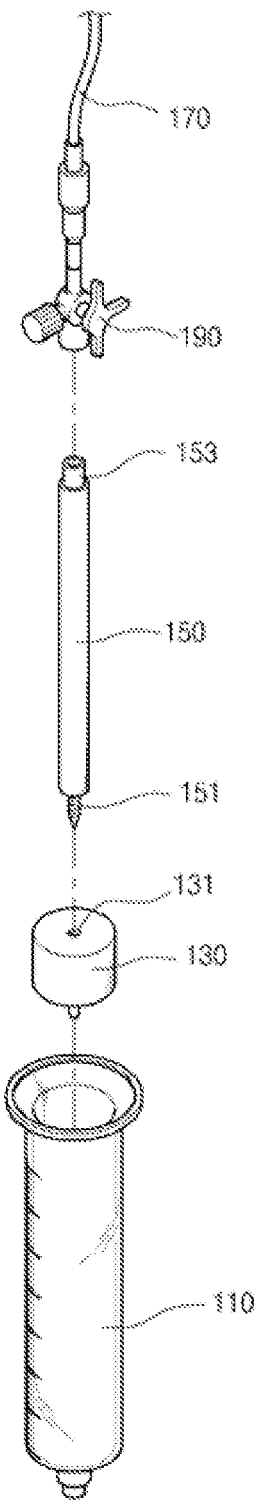
FIG. 2 is an exploded perspective view of an apparatus for implementing a method according to a preferred embodiment of the present invention.
Figure 3:
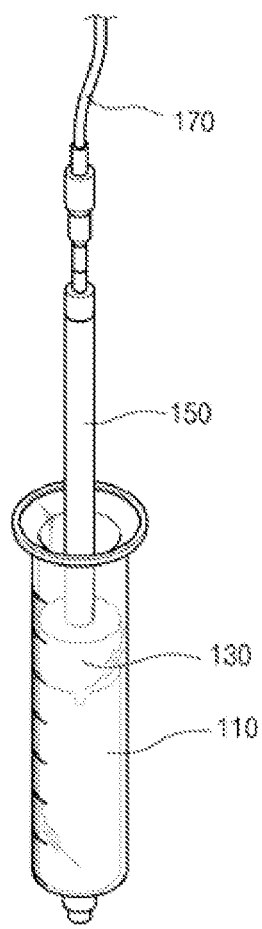
FIG. 3 is a perspective view of an apparatus for implementing a method according to another embodiment of the present invention.
Figure 4:
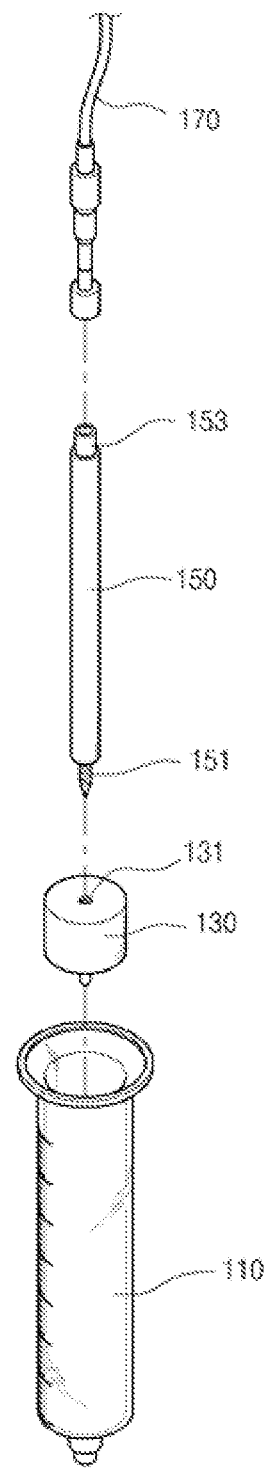
FIG. 4 is an exploded perspective view of an apparatus for implementing a method according to another embodiment of the present invention.

The terms "about," "substantially," etc. as used herein are intended to allow some leeway in mathematical exactness to account for tolerances that are acceptable in the trade and to prevent any unconscientious violator from unduly taking advantage of the disclosure in which exact or absolute numerical values are given so as to help understand the invention.

Hereinafter, an explanation will be given regarding methods of the present invention and apparatuses for implementing the methods. Fat is used in the methods and apparatuses, but it is merely illustrative. Examples of tissue types usable in the present invention include, but are not limited to, adipose tissue, blood, bone marrow, muscle, skin, liver, connective tissue, fascia and other soft fluid tissues or tissue ingredients.

The term "aspirate" as used herein is intended to include all substances obtained by liposuction. Typically, the aspirate includes adipose tissue and substances sucked out by liposuction.

First, the methods of the present invention use fat as a starting material, which can be obtained by liposuction. The fat may be one derived from humans. Alternatively, the fat may be autologous fat that can be cultured into adipose-derived stem cells, which are used for plastic surgery, etc. On the other hand, liposuction may be performed at a desired site. The fat may be sampled through a syringe. Any syringe capable of fat sampling may be used in the methods of the present invention, and non-limiting examples thereof include all kinds of syringes, such as those disclosed in Korean Patent Application Nos. 2003-5029, 2005-61134, 2005-34848 and 2006-64946, and Korean Utility Model Nos. 2003-21484, 2004-10685 and 2006-26454, all of which were proposed by the present inventor. These syringes are characterized in that aspirates obtained by liposuction are protected from the atmosphere.

Only active ingredients can be extracted from the aspirate through centrifugation. Then, the active ingredients can be treated with collagenase. According to a conventional method, one end of a container containing an aspirate must be opened for enzymatic treatment and washing solution feeding. In this course, the aspirate is exposed to the atmosphere, losing its stability.

In contrast, the methods of the present invention use a piston 130 having an outer diameter corresponding to the inner diameter of a container 110 containing an aspirate to minimize the exposure of the aspirate to the atmosphere. The piston has at least one through-hole 131. A connection tube 150 is adapted to feed an enzyme or a washing solution into the container 110 through the through-hole 131. The connection tube 150 has a tip 151 connected to the through-hole 131 and is connected to another container containing the enzyme or washing solution at the other end thereof.

The connection tube 150 may be connected to another container through an additional tube for convenience in use. Means for quantification control or a valve optionally connected to at least one container is provided in a zone where the connection tube 150 is connected to the another container. Non-limiting examples of the valve include a diaphragm one-way valve or a 3-way valve with Luer Lock 190. The valve may be manually or automatically operated.

In order to allow the enzyme or washing solution to enter the container containing the aspirate, the piston is pulled backward to form a negative pressure in the container. As a result of this depressurization, the enzyme or washing solution can be fed into the container through the connection tube and the through-hole of the piston.

Active ingredients, such as stem cells, are isolated from the mixture of the aspirate and the washing solution, etc. by centrifugation. Ingredients other than the active ingredients must be removed from the container. The removal procedure may be carried out in the reverse order to that of the feeding procedure. That is, the piston is pushed forward to form a positive pressure in the container. This pressurization allows a fluid rising in the piston to escape outside through the through-hole and the connection tube. The other end of the connection tube or the tube may be already connected to another container adapted to accommodate ingredients to be removed.

In the case where the three-way valve is provided, the active ingredients only can be extracted into another container (for example, a syringe) after ingredients other than active ingredients are optionally removed from the container. The three-way valve may also be connected to the container containing the washing solution, etc. That is, the 3-way valve includes: a first valve connected to the connection tube or the tube; a second valve connected to the container containing the washing solution or the container adapted to extract the active ingredients; and a third valve connected to the container adapted to extract the ingredients to be removed or the container containing the washing solution. This connection structure is given for illustrative purpose only and the present invention is not limited thereto.

When the washing procedure is repeated several times to isolate the stem cells, the opportunity for the active ingredients to be exposed to the atmosphere can be further minimized. The syringe used for liposuction may be used as the container containing the aspirate.

Although the present invention has been described herein with reference to the foregoing embodiments and accompanying drawings, the scope of the present invention is not limited to the embodiments and drawings. Therefore, it will be evident to those skilled in the art that various substitutions, modifications and changes are possible, without departing from the spirit of the invention as disclosed in the accompanying claims.

The invention claimed is:

1. A method for isolating stem cells using an apparatus comprising: a container containing an aspirate comprising stem cells; a piston having an outer diameter corresponding to the inner diameter of the container and having at least one through-hole; and a connection tube adapted to feed an enzyme or a washing solution into the container through the through-hole, having a tip connected to the through-hole, and connected to an external tube or another container containing the enzyme or washing solution at the other end thereof,
wherein the method comprises:
pulling the piston backward to form a negative pressure in the container containing the aspirate to allow the enzyme or washing solution to enter the container containing the aspirate through the connection tube and the through-hole of the piston,
performing centrifugation to isolate stem cells as active ingredients from the mixture of the aspirate and the enzyme or washing solution, and
after centrifugation is performed pushing the piston forward to form a positive pressure in the container and to allow a fluid rising in the piston to escape outside through the through-hole and the connection tube,
whereby the container with the isolated stem cells remains.

2. The method according to claim 1, wherein the connection tube is connected to another container through the external tube.

3. The method according to claim 2, wherein the apparatus further comprises means for quantification control or a valve optionally connected to at least one container proximate to the connection tube.

4. The method according to claim 3, wherein the valve is a diaphragm one-way valve or a 3-way valve with Luer Lock.

5. The method according to claim 4, wherein the 3-way valve alternatively connects said other end of the connection tube to a container containing the washing solution or enzyme via the external tube or to a container adapted to extract active ingredients.

6. The method according to claim 1 further comprising repeating the washing procedure several times to isolate the stem cells.

7. The method according to claim 1 further comprising recovering the isolated stem cells from the container.

8. The method according to claim 4, wherein the 3-way valve is connected to said other end of the connection tube, the external tube connected to a container containing the washing solution or enzyme and another container adapted to extract active ingredients.

* * * * *